United States Patent [19]
Conkright

[11] Patent Number: 5,850,344
[45] Date of Patent: Dec. 15, 1998

[54] MEDICATION DISPENSING AND TIMING SYSTEM

[75] Inventor: Gary W. Conkright, Naperville, Ill.

[73] Assignee: Profile Systems, LLC, Merrillville, Ind.

[21] Appl. No.: 514,989

[22] Filed: Aug. 14, 1995

[51] Int. Cl.[6] .................................................. G06F 9/00
[52] U.S. Cl. .............................. 364/479.01; 364/479.11;
364/479.14; 340/286.07; 340/311.1; 221/1;
221/2; 221/9; 221/3
[58] Field of Search ........................ 364/479.01, 479.03,
364/479.07, 479.11, 479.12, 479.14, 478.01,
478.03, 478.04, 478.06, 478.09, 478.12–478.15,
138, 140, 143, 185, 550, 551.01, 569, 413.01,
413.02, 148, 479.02; 221/1, 2, 5, 7, 9, 11,
13, 15, 3, 8, 22, 30, 31; 340/825.44–825.47,
825.72, 286.07, 311.1

[56] References Cited

U.S. PATENT DOCUMENTS

| | | | |
|---|---|---|---|
| 3,193,196 | 7/1965 | Merrill et al. | 235/98 |
| 3,206,062 | 9/1965 | Rappaport | 221/7 |
| 3,215,310 | 11/1965 | Hurst et al. | 221/7 |
| 3,266,664 | 8/1966 | Pearson et al. | 221/7 |
| 3,368,713 | 2/1968 | Hurst et al. | 221/7 |
| 3,558,004 | 1/1971 | Boyd, Jr. | 221/7 |
| 3,772,740 | 11/1973 | List | 221/7 |
| 3,823,844 | 7/1974 | Linkemer et al. | 221/13 |
| 3,837,139 | 9/1974 | Rosenberg | 53/59 R |
| 3,871,156 | 3/1975 | Koenig et al. | 53/59 R |
| 3,997,063 | 12/1976 | Adams et al. | 214/1 C |
| 4,013,192 | 3/1977 | Pillon | 221/7 |
| 4,018,358 | 4/1977 | Johnson et al. | 221/7 |
| 4,094,129 | 6/1978 | List | 53/54 |
| 4,111,332 | 9/1978 | Hurst et al. | 221/7 |
| 4,171,065 | 10/1979 | Hurst | 221/7 |
| 4,396,828 | 8/1983 | Dino et al. | 377/6 |
| 4,504,153 | 3/1985 | Schollmeyer et al. | 364/479.14 |
| 4,733,362 | 3/1988 | Haraguchi | 364/479 |
| 4,809,880 | 3/1989 | Stein | 221/204 |
| 4,869,394 | 9/1989 | Hurst | 221/7 |
| 4,870,799 | 10/1989 | Bergerioux et al. | 53/55 |
| 4,932,559 | 6/1990 | Stein | 221/7 |
| 4,953,745 | 9/1990 | Rowlett, Jr. | 221/5 |
| 4,984,709 | 1/1991 | Weinstein | 221/7 |
| 5,208,762 | 5/1993 | Charhut et al. | 364/478 |
| 5,319,355 | 6/1994 | Russek | 340/311.1 |
| 5,329,459 | 7/1994 | Kaufman et al. | 364/479.11 |
| 5,337,919 | 8/1994 | Spaulding et al. | 221/2 |
| 5,347,453 | 9/1994 | Maestre | 364/413.01 |
| 5,348,061 | 9/1994 | Riley et al. | 141/104 |
| 5,405,048 | 4/1995 | Rogers et al. | 221/11 |
| 5,537,459 | 7/1996 | Price et al. | 340/286.07 |
| 5,582,323 | 12/1996 | Kurtenbach | 221/2 |
| 5,657,236 | 8/1997 | Conkright | 364/479.14 |

*Primary Examiner*—Edward R. Cosimano
*Assistant Examiner*—Hal P. Wachsman
*Attorney, Agent, or Firm*—Lockwood, Alex, FitzGibbon & Cummings

[57] ABSTRACT

A medication dispensing and timing system includes a central monitoring computer which generates and sends an address-specific medication prompting message in accordance with a prescribed medication dispensing schedule over a two-way paging system to a communicator carried by a patient. The communicator includes receiver circuitry which responds to the prompt message to generate a display and audible alarm to alert the patient. Upon the patient acknowledging the message by actuating a switch on the communicator transmitter circuitry within the pager sends a reply message to the monitoring computer. In the event that a reply message is not received within a predetermined time period following the dispensing event, the computer initiates an alternative communication procedure which includes telephone calls to 1) the patient, 2) his doctor, 3) his care provider, or 4) an emergency contact. The communicator may be equipped to electrically communicate with medication dispensing apparatus whereby the apparatus dispenses medication in response to a received prompting message. The dispensing apparatus may include a modem for communicating with the central monitoring computer to confirm actual dispensing, and to provide a control path whereby the dispensing apparatus can be controlled from the monitoring computer in the event of a radio link failure.

24 Claims, 3 Drawing Sheets

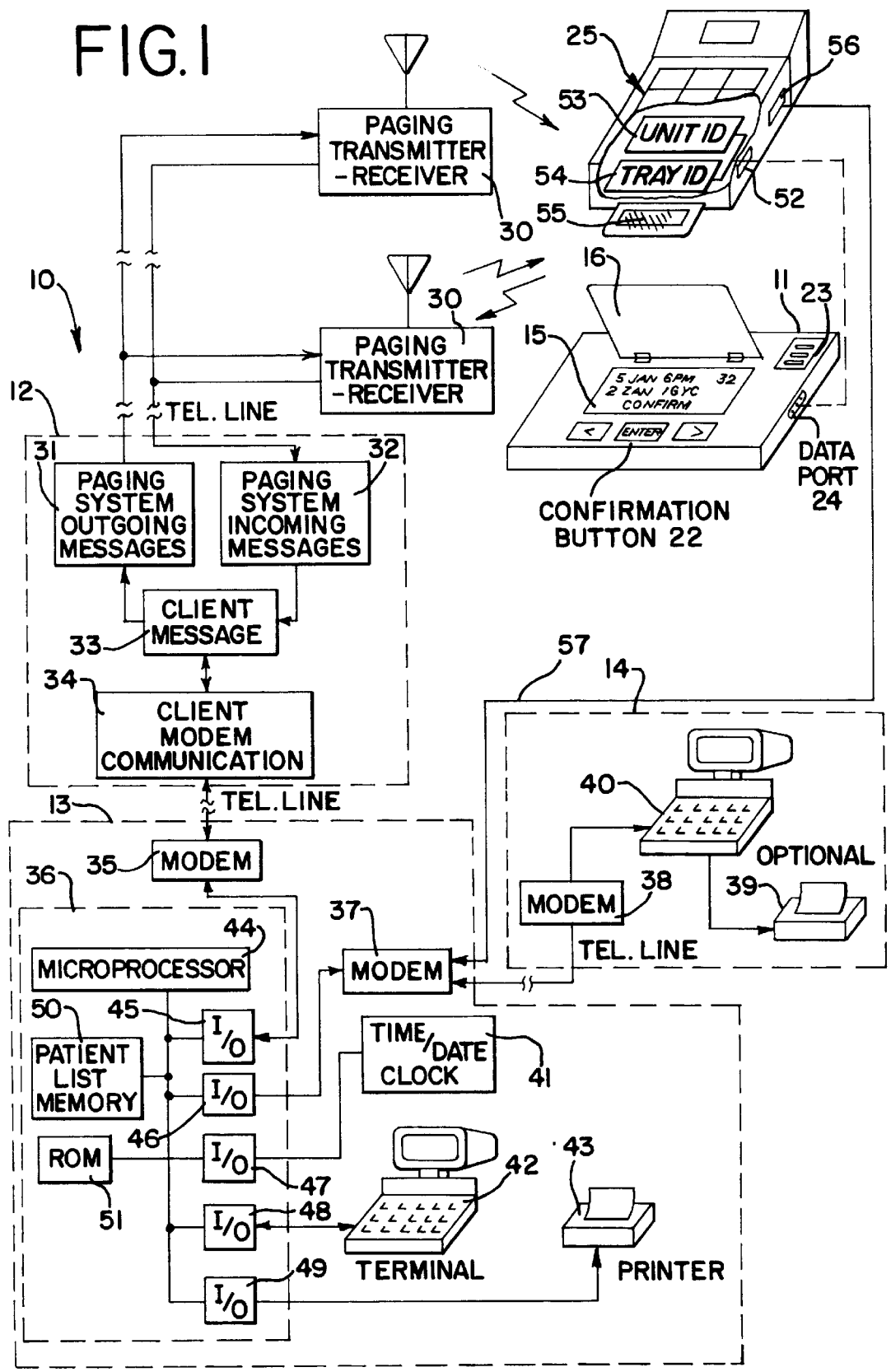

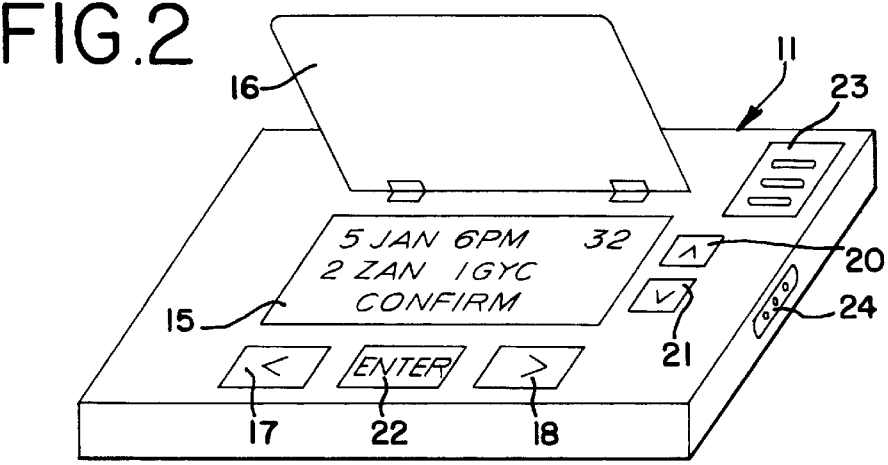
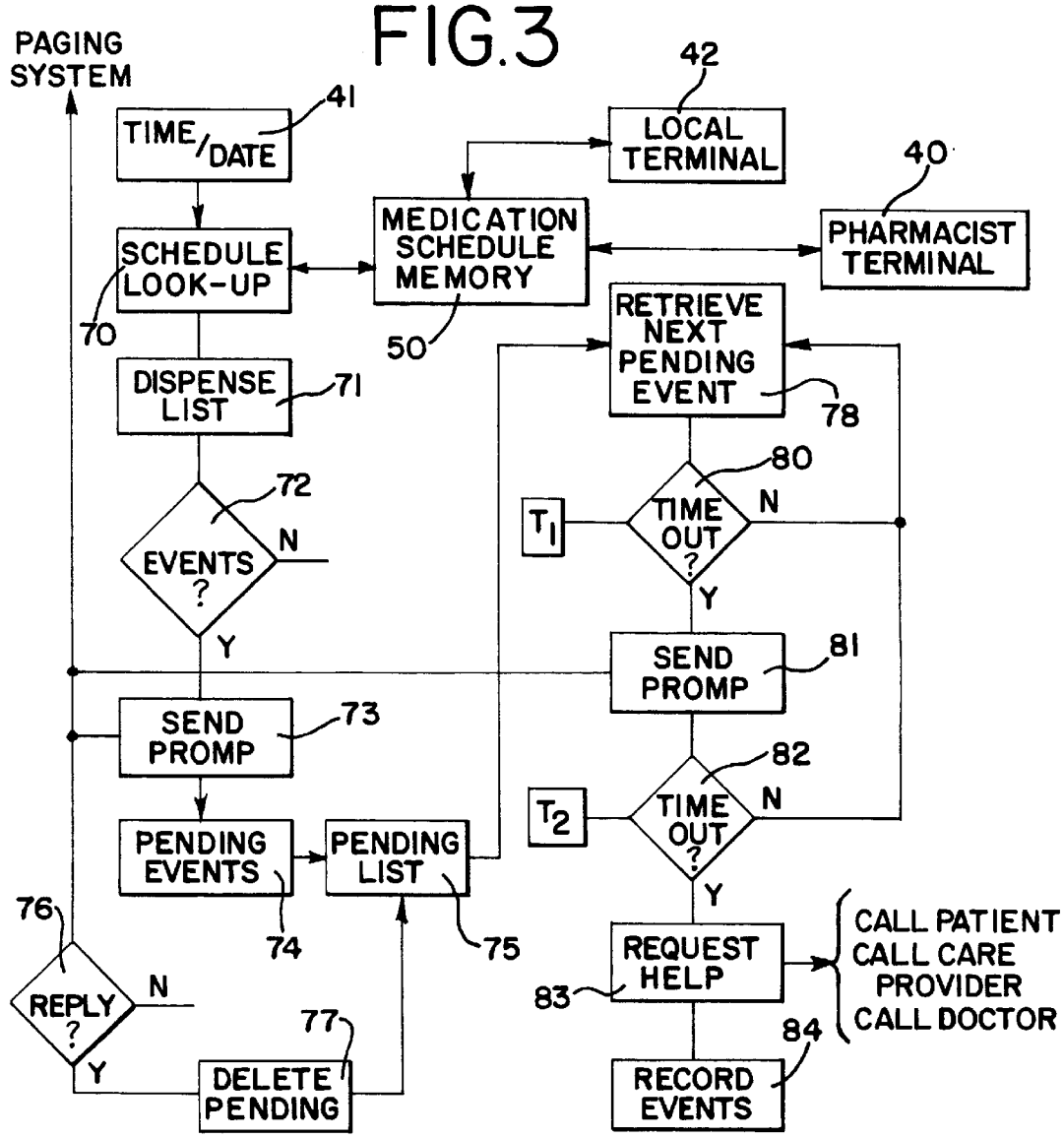

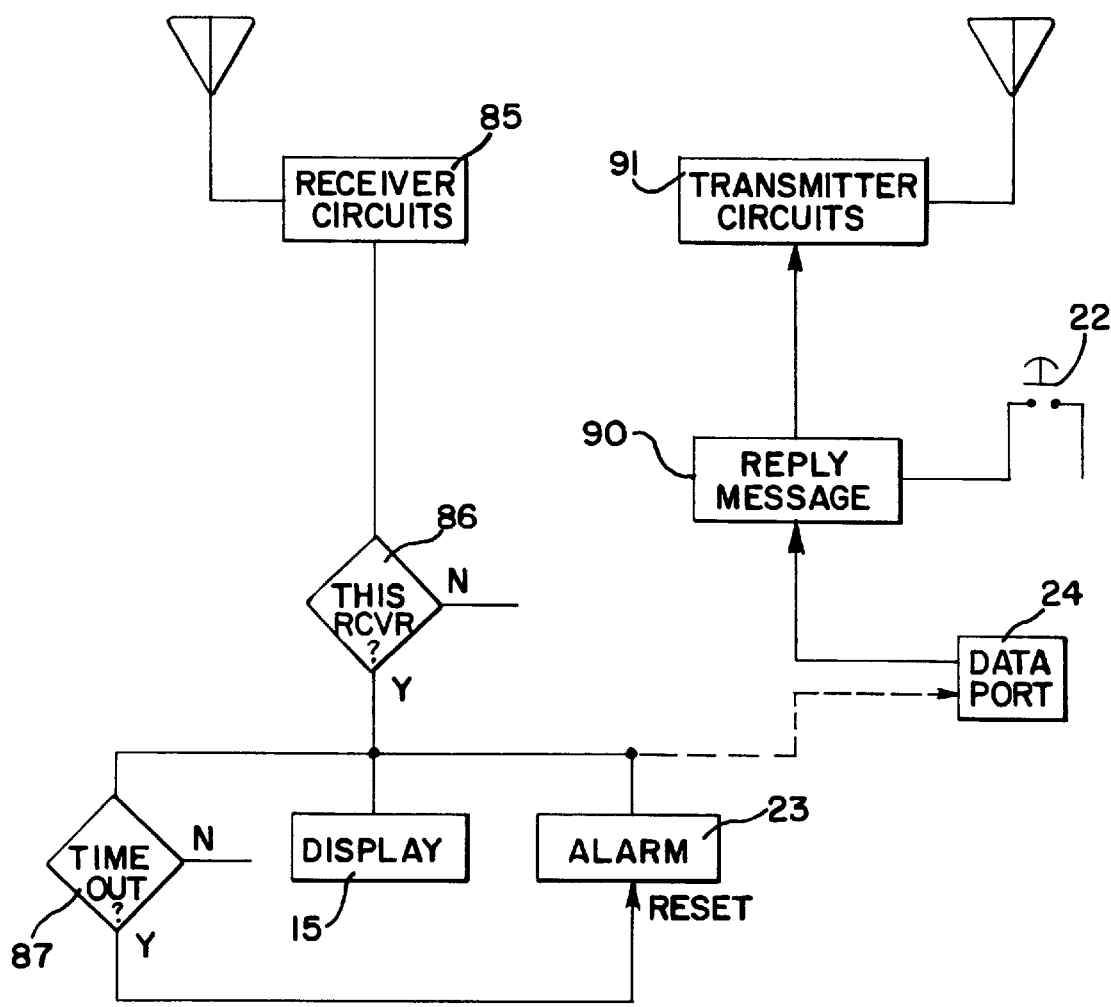

MEDICATION DISPENSING AND TIMING SYSTEM

BACKGROUND OF THE INVENTION

The present invention relates generally to medication dispensing systems, and more particularly to a medication dispensing system wherein a patient is prompted to take medication in accordance with a prescribed medication schedule by a communicator device carried on his person, and wherein the patient acknowledges receipt of the prompt by causing the communicator to send a reply message to a computer at a central monitoring facility. A supplemental notification procedure is initiated by the computer in the event that the reply message is not received within a predetermined period of time following the prescribed time for taking the medication.

In dispensing medication a primary problem has been recognized in prompting a patient to take a prescribed dose of medication at prescribed times. Patients are often preoccupied with other matters and may forget at the prescribed time. In the case of some geriatric patients, a loss of mental acuity may cause a lapse of memory or an extended period of forgetfulness, resulting in no medication or the wrong medication being taken.

Various apparatus have been developed for prompting a patient to take medication, including medication dispensers which incorporate a timer and/or dispensing means operable from the timer. An example of one such device is disclosed in U.S. Pat. No. 4,763,810, issued Aug. 16, 1988 which describes a motor-driven, tamper-proof automated medication dispenser. This dispenser has multiple compartments each holding a single dose of medication. A motorized delivery system controlled by a clock circuit removes a single dose from a specific compartment. An audio and visual alarm notifies the patient that a dose of medication is ready for taking. However, there are no means for monitoring whether the patient has actually removed the medication from the dispenser.

U.S. Pat. No. 4,223,801, issued Sep. 23, 1980, describes an automated medication dispenser which is equipped with an alarm for alerting a patient when medication is to be taken. A remote alarm is activated upon reception of a paging signal by the dispenser indicating that it is time to take medication, the signal being terminated when the medication is removed from the dispenser. Although this dispenser can be activated remotely by a third party, it only alerts the patient that it is time to take medication and has no provision for confirming that the patient has or has not taken the medication.

These prior art devices do not permit monitoring of a dispensing schedule at a remote location, nor do they remind a patient away from the dispenser that it is time to take medication. A need therefore exists for an automated medication dispensing system which alerts a patient in the course of his daily activities to take specific medication and which confirms that the patient has taken the medication, whereby the medication schedule of the patient can be monitored by computer at a central monitoring facility.

The present invention meets this need by providing a medication dispensing and timing system in which a radio frequency receiver receives coded signals from the monitoring office and is activated to sound an alarm and provide a display according to a preassigned medication dispensing schedule. The patient confirms the prompt by actuating a transmitter, which generates a signal which is received at the monitoring office.

In the event that a reply message is not received at the central monitoring computer within a predetermined period of time following a scheduled medication event, a follow-up individually addressed prompt message is sent to the particular patient communicator. In the event that this message is not responded to, a supplemental communicator procedure is initiated where help is obtained by telephone.

The present invention preferably includes a two-way personal communicator incorporating a receiver and transmitter which is carried by the patient and which receives and decodes signals transmitted from a central monitoring facility to advise the patient of the need to take medication in accordance with a prescribed schedule, and which transmits a reply signal to the monitoring facility indicating that the prompt has been received. In the absence of a reply signal, the central monitoring facility sends a further prompt signal and initiates a supplemental procedure to secure help.

Also, the dispensing apparatus may be provided with a telephone modem whereby actual operation of the apparatus can be monitored at the central computer and whereby the apparatus can be controlled by the central computer in the event of paging system failure.

Accordingly, it is a general object of the present invention to provide a new and improved medication dispensing and timing system.

It is a further object of the present invention to provide a wireless medication dispensing and timing system in which a patient is prompted to take medication in accordance with a prescribed medication dispensing schedule.

It is another object of the present invention to provide a medication dispensing and timing system responsive to control signals generated by a central monitoring facility in which the patient is prompted in accordance with a prescribed medication schedule, and in which an acknowledgment that the patient received the prompt is transmitted back to the monitoring facility, and in which an alarm is sounded when the patient has not acknowledged the prompt within a predetermined period of time following the prompt.

It is a further object of the present invention to provide a medication dispensing and timing system that utilizes a dispenser to provide a dose of medicine according to a medication schedule. The dispenser communicates through the use of a paging system as well as a backup phone line communication network. An alarm signal is generated by the monitoring computer when the dispensed dose of medication is not removed from the dispenser within a predetermined time period. Also, the dispenser keeps a detailed record of what types of medication were dispensed at what time, and when they were removed.

It is a more specific object of the present invention to provide an improved medication dispensing and timing system whereby a two-way paging system is utilized to transmit prompting messages from a central monitoring facility to individual paging receivers to provide a prompt. The medication schedule may be conveyed to the monitoring facility by a pharmacist or other entity licensed to dispense medication by means of a computer terminal at the pharmacy and a telephone line connection between the terminal and the monitoring computer. When a push-button switch is activated by the patient, the communicator generates a confirmation signal which is sent to the monitoring computer to confirm that the prompt has been received by the patient. An alarm signal is generated by the monitoring computer when an acknowledgment is not received from the pager within a predetermined time period following receipt of a dispensing command signal.

SUMMARY OF THE INVENTION

The invention is directed to a medication dispensing and timing system comprising central monitoring means for generating a prompt signal for each dosage of medication called for by a predetermined medication schedule associated with a particular patient, a communicator including a uniquely addressed receiver associated with the particular patient having means for prompting the patient to take each predetermined dose of medication. A wireless communication network for conveying the prompt signal to the uniquely-addressed receiver. The communicator may further include transmitter means responsive to an external control effect for generating a reply signal acknowledging receipt of the prompt signal. An additional wireless communication network conveys the reply signal to the central monitoring means, and the central monitoring means includes alarm generating means responsive to the reply signal for initiating a predetermined follow-up procedure in the absence of the reply signal following the lapse of a predetermined time period following the prompt signal.

The invention is further directed to a medication dispensing system operable over a two-way paging system, the dispensing system comprising central monitoring means for generating a prompt signal for each dose of medication called for by a predetermined medication schedule associated with a particular patient, a patient communicator including a uniquely addressed receiver associated with the patient having means for prompting the patient to take each predetermined dose of medication, the patient communicator further including transmitter means responsive to an external control effect for generating a reply signal acknowledging receipt of the prompt signal, and the central monitoring means including alarm generating means responsive to the reply signal for initiating a predetermined follow-up procedure in the absence of the reply signal following the lapse of a predetermined time period following the prompt signal.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a simplified functional block diagram of a medication dispensing and timing system constructed in accordance with the invention.

FIG. 2 is an enlarged perspective view of a patient communicator utilized in the medication dispensing and timing system of FIG. 1.

FIG. 3 is a simplified flow chart illustrating the operation of the central monitoring computer of the medication dispensing and timing system of FIG. 1.

FIG. 4 a simplified flow chart illustrating the operation of the patient communicator utilized in the medication dispensing and timing system of FIG. 1.

DESCRIPTION OF THE PREFERRED EMBODIMENT

Referring to the Figures, and particularly to FIGS. 1 and 2, a medication dispensing and timing system 10 constructed in accordance with a preferred embodiment of the invention for prompting multiple patients having different medication schedules to take medication includes a two-way personal patient communicator 11 associated with each patient, a two-way wireless communication system 12, a single central monitoring facility 13 and a plurality of pharmacist stations 14.

Referring to FIG. 2, the patient communicator 11 is seen to include a display screen 15 on which an alpha-numeric message is displayed. Typically, this message may indicate the time and date of a prescribed medication event, the reference number of that event, and optional detail as to which medications are included in the event. A hinged cover 16 may be provided to cover screen 15 when the communicator 11 is not in use.

To allow for patient input the communicator may include a pair of left-right cursor keys 17 and 18 and a pair of up-down cursor keys 20 and 21. An enter key 22 functions as a confirmation key in accordance with indicia on display screen 15 to enable the patient to confirm receipt of a medication prompt on the screen. An alarm 23 may be incorporated in communicator 11 to audibly alert the patient of the need to take medication, and a data port 24 may be optionally provided to enable data to be exchanged between the communicator and another device, such as a medication dispensing apparatus 25 (shown in FIG. 1).

In a manner well known to the art, paging messages may be supplied to communicator 11 by a plurality of paging 30, each incorporating transmitting and receiving means whereby radio signals are transmitted to and received from communicator 11. These messages are typically conveyed to and from paging sites 30 by means of telephone lines or microwave links to a paging system control center 12. Within this center an outgoing message control circuit 31 controls the coding, timing and routing of outgoing messages, and an incoming message control circuit 32 controls the coding, timing and routing of incoming messages. Conventional techniques may be utilized within the paging network control system 12, including a client communication circuit 33 and modem 34, to establish communication over a telephone line or other communication link with the monitoring facility 13.

Within monitoring facility 13 messages to and from the paging network are processed by a modem 35, which communicates with a monitoring computer 36. Computer 36 also communicates with each pharmacist station 14 through a modem 37 within monitoring facility 13. Modem 37 is connected by a telephone line or equivalent communication link to a modem 38 within the pharmacist station and a conventional terminal 40. This terminal enables the pharmacist to retrieve and input information regarding a particular patient medication dispensing schedule, including the time of each patient reply.

Monitoring computer 36 also receives time and date information from a clock circuit 41. A terminal 42 is connected to monitoring computer 36 to enable an operator at the monitoring facility to selectively page a particular patient, to call up the medication dispensing history of a particular patient, or to review and/or modify the medication schedule of a particular patient. A printer 43 allows for the generation of written reports and documentation as required in the operation of the monitoring center.

Monitoring computer 36 may be conventional in structure and operation. In particular, the computer may include a conventional microprocessor 44, a plurality of input-output circuits 45–49, a memory 50 for storing patient medication dispensing schedules and other information, and a ROM 51 for storing the operating program and other required system information.

In operation, messages addressed to individual patient communicators 11 are generated within monitoring computer 36 as required by the particular patient's medication schedule. In particular, at the time medication is called for by the medication schedule monitoring computer 36 generates a message addressed to the communicator 11 of that particular patient conveying the date and time, the consecutive number of the particular medication event, and optionally detail as to the composition of the event. In the illustrated example the event occurred on Jan. 5, 1995 at 6:00 p.m. and was event number 32 on this schedule. Two pills of a first medication identified as "ZAN" and 1 pill of a medication identified as "GYC" are called for. An acknowledgment by the patient is requested.

The message generated by monitoring computer 36 is addressed specifically to a single communicator 11, and is conveyed through modems 35 and 34, and communications manager circuit 33 to the outgoing message management circuit 31. From there the message is conveyed to paging sites 30 for transmission to the specific communicator 11. In the case of a two-way system as shown, the system 12 may be knowledgeable as to the whereabouts of the addressed communicator and therefore may need only provide an outgoing message at the paging site 30 closest to the communicator.

Communicator 11 displays an alpha-numeric message as shown. The audible alarm 23 is sounded to alert the patient to review the message. Upon reviewing the message, the patient depresses switch 22, causing the communicator to send a message to monitoring computer 36 by way of the paging system site 30, the incoming message control circuit 32, client message control circuit 33 and modems 34 and 35.

In accordance with the invention, monitoring computer 36 initiates an alert routine in the event that a reply message is not received from communicator 11 within a predetermined period of time $T_1$ following a time of the last medication event. For example, if $T_1$ is 10 minutes, and if medication is prescribed to be taken at 6:00 p.m. and no response has been received from communicator 11 by 6:10 p.m., monitoring computer 36 initiates another medication prompting message to communicator 11 for the purpose of reminding the patient that he still has not taken his prescribed medication. If a reply is not received in a further predetermined time period $T_2$, say two minutes, the operator at monitoring facility 13 is alerted through terminal 42 and printer 43 of a non-responsive condition. At this time, a telephone call may be made to 1) the patient, 2) the patient's care providing facility, 3) the patient's physician, 4) the drug filling the prescription, or 5) another person designated to physically check up on the patient. These telephone calls are duly logged and if necessary emergency agencies can be contacted for further assistance.

The medication dispensing apparatus 25 may be optionally included in medication dispensing system 10. In this instance, to dispense medication from apparatus 25 it is necessary that the data port 24 of communicator 11 be connected with a data port 52 on apparatus 25. This connection having been made, a unit ID circuit 53 and cassette ID circuit 54 within dispenser 25 may require a match with unit and cassette ID numbers included in the medication prompting message. Only in the event of such a match, will dispenser 25 dispense medication to the patient. This precludes the patient from inadvertently taking dangerous multiple doses of medication by repeatedly actuating the dispensing apparatus.

Also, communicator 11 may be programmed to transmit a confirmation signal only upon medication dispenser 25 providing a signal at data port 24 which indicates that the medication has in fact been dispensed and removed from a hopper 55 of the dispenser.

The medication dispensing apparatus 25 may include a modem 56 for connection to a telephone line 57, which corrects the dispenser to modem 37 at the central monitoring facility. This communication link may be used for confirming actual operation of the apparatus to monitoring computer 36, or by computer 36 to control the dispensing apparatus in the event of failure of the paging system.

The operation of the medication dispensing system 10 is illustrated in FIGS. 3 and 4. There it is seen that the time and date output of clock circuit 41 is utilized in a table look-up operation 70 to determine whether a medication dispensing event is called for in any of the medication schedules stored within the system memory 50. Medication schedules stored within memory 50 may be monitored, modified or deleted at any time by inputs from either the local terminal 42 or any of the pharmacist terminals 40. In practice, appropriate safe guards may be provided to prevent a pharmacist from modifying or deleting selected patient medication schedules, including patient medication schedules with which he is not involved.

In the event the schedule look-up procedure 70 identifies one or more medication events to be accomplished at the then existing time and date a dispense list is formed at 71 containing the medication events to be accomplished. If it is established that one or more such events exist at 72 a prompt message addressed to each particular patient's communicator 11 is prepared and sent at 73. At the same time, at 74 a list of pending events is formed for storage in a pending list memory 75. The process then continues with the next event.

In the event that a reply is received from a patient communicator 11, the reply is recognized at 76 and caused at 77 to delete that particular pending event from the pending list 75. At the same time, each medication event on pending list 75 is retrieved at 78 for possible further action. In the event that a period of time in excess of the predetermined time interval $T_1$ has elapsed since the pending event as determined at 80, a follow-up prompt is generated and sent at 81. In the event that the time period has not been exceeded, the next subsequent pending event is retrieved at 78 for evaluation.

In the event that the follow-up prompt generated at 81 is not followed by a reply within a second predetermined time interval $T_2$ as determined at 72, a routine is begun at 83 which may include further follow-up prompt messages, a call to the patient, a call to the patient's care provider, a call to the patient's doctor, a call to the patient's pharmacist or a call to some designated individual. All such events are recorded at 84 within the monitoring computer of the system.

Referring to FIG. 4, within communicator 11 receiver circuits 85 derive digital messages which are analyzed at 86 to determine whether the incoming message is for the particular communicator. In the event that it is, the message is displayed on display screen 15 and the audible alarm 23 is sounded. After a period of time determined at 87 alarm 23 is reset pending receipt of another message.

Acknowledgment of the prompting message is initiated by the patient actuating switch 22, which causes a reply message including the communicator address to be generated at 90 for transmission by transmitter circuitry 91 within the communicator to the medication dispensing and timing monitoring center 13. There, the reply message is utilized in the manner previously described to account for completion of the medication event.

In the event that the system is provided with medication dispenser 25, incoming messages are provided through data port 24 and completion of the dispensing operation is indicated through data port 24 for initiation of a reply message at 90.

It will be appreciated that various safe guards can be incorporated into the system. For example, a discrete code may be included in each prompt message for comparison to an identical discrete code stored within the communicator. Only in the event of a match of these codes will the message be recognized. Similarly, a discrete code may be required in each reply message to verify the authenticity of the reply signal. As previously developed, in the case of dispensing apparatus 25 it may be necessary that an electronic serial number of the apparatus and the removable medication cassette utilized therein match before the apparatus will respond to a medication prompt message or provide a reply indicative that dispensing has occurred. Furthermore, communications between the paging system 12 and the monitoring facility 13, and between the pharmacist station 14 and the monitoring facility 13 may be encrypted or otherwise protected by similar coding to confirm authenticity.

Alternatively, in the event a one-way paging system is utilized, confirmation of receipt of the prompt signal, and optionally actual dispensing of the prescribed medication, may be accomplished by sending a suitable confirmation signal from dispenser 25 to monitoring computer 36 over telephone line 57.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. A medication dispensing system comprising:
   central monitoring means for generating a prompt signal for each dosage of medication called for by a predetermined medication schedule associated with a particular patient;
   a communicator including a uniquely addressed receiver associated with said patient having means for prompting said patient to take each predetermined dose of medication;
   a wireless communication network for conveying said prompt signal to said uniquely-addressed receiver;
   said communicator further including transmitter means responsive to an external control effect for generating a reply signal acknowledging receipt of said prompt signal;
   an additional wireless communication network for conveying said reply signal to said central monitoring means; and
   said central monitoring means including alarm generating means responsive to said reply signal for initiating a predetermined follow-up procedure in the absence of said reply signal following the lapse of a predetermined time period following said prompt signal.

2. A medication dispensing system as defined in claim 1 wherein said wireless communication network is a paging system, and said communicator is a two-way paging receiver.

3. A medication dispensing system as defined in claim 1 wherein said external control effect comprises a patient-actuable switch.

4. A medication dispensing system as defined in claim 1 wherein said patient prompting means comprise an alphanumeric display viewable by the patient.

5. A medication dispensing system as defined in claim 1 wherein said patient prompting means comprise a patient-audible alarm.

6. A medication dispensing system as defined in claim 1 wherein said system includes a medication dispenser operable from said communicator whereby a predetermined dose of medication is dispensed according to a predetermined medication schedule.

7. A medication dispensing system as defined in claim 6 wherein said dispenser includes communication means for communicating with said receiver and producing a confirmation signal indicative of the dispensing of a dose of medication, and also if said dose of medication was taken from a hopper of said medication dispenser and said control effect is generated by said dispensing apparatus following receipt of said confirmation signal by said medication dispenser.

8. A medication dispensing system as defined in claim 6 wherein said dispenser includes memory means for receiving dispensing instructions from said receiver.

9. A medication dispensing system as defined in claim 6 wherein said dispenser includes memory means for keeping a detailed record of when the medication is taken.

10. A medication dispensing system as defined in claim 6 wherein a signal sent to said dispenser by said communicator includes a unique address associated with said dispenser, and said dispenser is responsive only to signals conveying said unique address.

11. A medication dispensing system as defined in claim 6 wherein said central monitoring means includes a monitoring computer, and said system includes at least one pharmacist terminal located remote from said monitoring means for conveying a patient medication schedule to the monitoring means.

12. A medication dispensing system as defined in claim 11 wherein said pharmacist terminal further conveys a unique address associated with said dispenser to said central monitoring means.

13. A medication dispensing system as defined in claim 1 wherein said central monitoring means includes a monitoring computer, and said system includes at least one pharmacist terminal located remote from said monitoring means for conveying a patient medication schedule to the monitoring means.

14. A medication dispensing system operable over a two-way paging system, said dispensing system comprising:
   central monitoring means for generating a prompt signal for each dose of medication called for by a predetermined medication schedule associated with a particular patient;
   a patient communicator including a uniquely addressed receiver associated with said patient having means for prompting said patient to take each predetermined dose of medication;
   said patient communicator further including transmitter means responsive to an external control effect for generating a reply signal acknowledging receipt of said prompt signal;
   a modem for telephone line communication between a dispenser and said central monitoring means for confirmation of dispensing to said central monitoring means and control of said dispenser by said central monitoring means; and
   said central monitoring means including alarm generating means responsive to said reply signal for initiating a predetermined follow-up procedure in the absence of said reply signal following the lapse of a predetermined time period following said prompt signal.

15. A medication dispensing system as defined in claim 14 further including a wireless communication system which comprises a paging system, and said patient communicator is a two-way paging receiver.

16. A medication dispensing system as defined in claim 14 wherein said external control effect comprises a patient-actuable switch.

17. A medication dispensing system as defined in claim 14 wherein said patient prompting means comprise an alphanumeric display viewable by the patient.

18. A medication dispensing system as defined in claim 14 wherein said patient prompting means comprise a patient-audible alarm.

19. A medication dispensing system as defined in claim 14 wherein said system includes a medication dispenser having communication means for communicating with said receiver and producing a confirmation signal indicative of the dispensing of a dose of medication, and said control effect is generated by said dispensing apparatus following receipt of said confirmation signal by said medication dispenser.

20. A medication dispensing system as defined in claim 19 wherein said dispenser includes memory means for receiving dispensing instructions from said receiver.

21. A medication dispensing system as defined in claim 20 wherein said dispensing instructions includes a unique address associated with said dispenser, and said dispenser is responsive only to signals conveying said unique address.

22. A medication dispensing system as defined in claim 19 wherein said central monitoring means includes a monitoring computer, and said system includes at least one pharmacist terminal located remote from said monitoring means for conveying a patient medication schedule to the central monitoring means.

23. A medication dispensing system as defined in claim 22 wherein said pharmacist terminal further conveys a unique address associated with said dispenser to said central monitoring means.

24. A medication dispensing system as defined in claim 14 wherein said central monitoring means includes a monitoring computer, and said system includes at least one pharmacist terminal located remote from said monitoring means for conveying a patient medication schedule to the central monitoring means.

* * * * *